United States Patent [19]

Plotkin et al.

[11] Patent Number: 5,095,124
[45] Date of Patent: Mar. 10, 1992

[54] PROCESS FOR THE PREPARATION OF ALK-1-ENYL ETHER CYCLOCARBONATE

[75] Inventors: Jeffrey S. Plotkin, Monsey, N.Y.; Mark M. Miller, Ridgewood; Paul D. Taylor, West Milford, both of N.J.

[73] Assignee: ISP Investments Inc., Wilmington, Del.

[21] Appl. No.: 582,033

[22] Filed: Sep. 10, 1990

[51] Int. Cl.$^5$ .................. C07D 407/00; C07D 301/00
[52] U.S. Cl. .................... 549/229; 549/228; 549/230; 549/540
[58] Field of Search ............. 549/229, 540, 228, 230

[56] References Cited

U.S. PATENT DOCUMENTS

| | | | |
|---|---|---|---|
| 2,522,680 | 9/1950 | Kropa et al. | 549/229 |
| 2,773,070 | 12/1956 | Lichtenwalter et al. | 549/230 |
| 2,907,774 | 10/1959 | MacPeek | 549/540 |
| 3,952,066 | 4/1976 | Glickman et al. | 549/540 |
| 3,966,636 | 6/1976 | Jenkins et al. | 549/540 |
| 4,314,945 | 2/1982 | McMullen et al. | 549/229 |
| 4,344,881 | 8/1982 | Strege et al. | 549/229 |
| 4,423,235 | 12/1983 | Burgard et al. | 549/229 |
| 4,658,041 | 4/1987 | Renga | 549/229 |
| 4,835,289 | 5/1989 | Brindöpke | 549/229 |
| 4,892,954 | 1/1990 | Brindöpke | 549/229 |

OTHER PUBLICATIONS

P. H. Dixnet et al., NATO ASI SER., ser. C. (1990) vol. 314, pp. 65-77.
S. Berkman et al., Catalysis, Inorganic and Organic p. 396 (1940).
Carless et al., CA94-83558c (1981).
Larock, Comprehensive Organic Transformations, p. 113, isomerization of alkenes.

*Primary Examiner*—Cecilia Shen
*Attorney, Agent, or Firm*—Marilyn J. Maue; Joshua J. Ward

[57] ABSTRACT

The present invention relates to a two-stage liquid phase process wherein an alk-2-enyl glycidyl ether having the formula

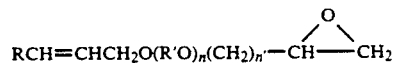

wherein R is hydrogen or lower alkyl; R' is $C_2$ to $C_4$ alkylene; n has a value of from 1 to 4 and n' has a value of from 0 to 4, is catalytically isomerized to the corresponding alk-1-enyl glycidyl ether in the first-stage of the reaction and the reaction mixture of the first-stage, containing the isomerization catalyst is then contacted with carbon dioxide in the presence of a phase transfer catalyst under a pressure ranging from atmospheric to about 400 psig in the second stage of the reaction.

6 Claims, No Drawings

PROCESS FOR THE PREPARATION OF ALK-1-ENYL ETHER CYCLOCARBONATE

BACKGROUND OF THE INVENTION

Glycidyl vinyl ethers have been used to produce the corresponding cyclocarbonate vinyl ethers which are said to have superior solvent properties and are capable of polymerization. However, this material is not commercially attractive since glycidyl vinyl ethers are difficult and costly to prepare. It is the aim of research to synthesize alk-1-enyl ether cyclocarbonates which possess all of the desirable properties of vinyl ether cyclocarbonates, but are more economical to prepare by a commercially acceptable process.

Accordingly it is an object of this invention to provide a process for the synthesis of alk-1-enyl ether cyclocarbonates in the absence of solvents or other extraneous by-products starting from commercially available starting materials.

Another object is to produce prop-1-enyl ether of propylene carbonate by a commercially feasible and economical process.

THE INVENTION

In accordance with one aspect of this invention the present process involves a two-stage liquid phase process wherein an alk-2-enyl glycidyl ether is catalytically isomerized to the corresponding alk-1-enyl glycidyl ether in the first-stage of the reaction and the reaction mixture of the first-stage, containing the isomerization catalyst, is then contacted with carbon dioxide in the presence of a phase transfer catalyst under a pressure ranging from atmospheric to about 400 psig in the second stage of the reaction.

The alk-2-enyl glycidyl ether of the process is one having the formula

wherein R is hydrogen or lower alkyl, R' is $C_2$ to $C_4$ alkylene, n has a value of from 0 to 4 and n' has a value of from 1 to 4.

The first-stage reaction is carried out in an unpressurized system at a temperature of between about 100° and about 155° C.; although higher temperatures, e.g. up to about 180° C. can be employed in a system under pressure of up to about 50 psig. The isomerization reaction is completed within a period of from about 2 to about 20 hours. Preferred conditions include reflux temperature under atmospheric pressure for 5 to 7 hours, during which greater than 98% yield of the alk-1-enyl glycidyl ether isomeric product is produced. The entire reaction mixture from the first-stage is then treated with carbon dioxide gas in the second-stage at a temperature of from about 100° to about 150° C. under a pressure of from about atmospheric to about 400 psig for a period of between about 1 and about 48 hours after which the alk-1-enyl ether cyclocarbonate is recovered in greater than 98% yield. Preferred conditions for the second-stage reaction include a temperature of between about 115° and about 135° C. under carbon dioxide pressure of from about 2 psi to about 200 psig for a period of 8 to 15 hours.

The first-stage reaction is carried out in the presence of between about 0.001 and about 1 wt. %, preferably between about 0.01 and about 0.1 wt. %, of a homogeneous or heterogeneous isomerization catalyst. Suitable homogeneous isomerization catalysts include ruthenium trichloride hydrate, ruthenium dioxide, triruthenium dodecarbonyl, ruthenium acetylacetonate, palladium chloride, palladium acetate, rhodium chloride, and the like. Suitable heterogeneous isomerization catalysts include supported ruthenium, palladium, or rhodium metal on alumina, carbon or silicas as the support.

The second-stage addition reaction is effected in the presence of between about 0.005 and about 5 wt. %, preferably between about 0.3 and about 3 wt. %, of a phase transfer catalyst such as a tetraalkyl ammonium halide, e.g. tetrabutyl ammonium bromide, tetraethyl ammonium iodide, a cyclic ether such as 18 crown 6 ether in conjunction with a potassium halide, e.g. iodide or bromide, or a bicyclic amino ether or bicyclic amine, such as triethylenediamine, with potassium iodide.

The combination of the isomerization and phase transfer catalysts in the second-stage reaction eliminates the need for multiple distillation operations since, in the present process, distillation is required only after completion of the second stage reaction to obtain greater than 98% product purity. Additionally, the combination of these two catalyst systems permits faster conversion to the cyclocarbonate product which is recovered in high purity.

The crude alk-1-enyl ether cyclocarbonate can be purified by any convenient method including flashing at reduced pressure, e.g. in a wiped film evaporator under 5-10 mm Hg. Any other purification method, e.g. carbon treatment, and/or water washing can be employed when additional product purification is desired.

The final product is a mixture of cis and trans alk-1-enyl ether cyclocarbonates containing less than 2% impurity.

The present products find utility as solvents for onium salts and thus, as reactive diluents for onium salt initiated systems in the curing of epoxy monomers or oligomers, of vinyl ether monomers or oligomers or mixtures containing acrylate monomers or oligomers.

Having generally described the invention, reference is now had to the following examples which illustrate preferred embodiments of the invention but which are not to be construed as limiting to its scope as more broadly defined above and in the appended claims.

EXAMPLE 1

Into a one-liter stainless steel autoclave is introduced 500 grams of allyl glycidyl ether (supplied by Alcolac Chemical Company) and 0.05 wt. % of ruthenium chloride hydrate. The resulting reaction mixture was heated to 154° C. for 6 hours after which greater than 98% yield of the corresponding prop-1-enyl glycidyl ether is produced. To this mixture at 125° C. is added 0.5 wt. % tetrabutyl ammonium bromide. Carbon dioxide is then pressured into the resulting mixture under a pressure of 300 psig for 12 hours, after which greater than 98% yield of the desired cis and trans mixture of the prop-1-enyl ether of propylene carbonate is produced. This product is treated in a wiped film evaporator at a temperature of 130° C. under 2 mm Hg (blade rpm 325) at a rate of 500 cc per hour, to produce the product in greater than 98% purity. A total yield of 92% is obtained.

What is claimed is:

1. A two-stage process for synthesizing alk-1-enyl ether cyclocarbonates from an alk-2-enyl glycidyl ether which comprises isomerizing an alk-2-enyl glycidyl ether in the presence of between about 0.001 and about 1 wt. % of an a ruthenium, rhodium or palladium isomerization catalyst at a temperature of between about 100° C. and about 180° C. under a pressure of from about atmospheric to about 50 psig to produce a catalyst/alk-1-enyl glycidyl ether mixture as an intermediate product and then reacting said mixture with carbon dioxide in the presence of between about 0.005 and about 5 wt. % of a halogen containing phase transfer catalyst at a temperature of between about 100° C. and about 150° C. under a pressure of from about atmospheric to about 400 psig to produce the corresponding alk-1-enyl ether cyclocarbonate as the product of the process.

2. The process of claim 1 wherein said isomerization catalyst is a homogeneous or a heterogeneous catalyst selected from the group of ruthenium dioxide, ruthenium trichloride hydrate, triruthenium dodecarbonyl, ruthenium acetylacetonate, palladium chloride, palladium acetate, rhodium chloride, ruthenium, palladium or rhodium metal supported on alumina carbon or silica and the phase transfer catalyst is selected from the group of a tetraalkyl ammonium halide, a cyclic crown ether in conjunction with potassium iodide, potassium bromide or a bicyclic amino ether or bicyclic amine in conjunction with potassium iodide or bromide.

3. The process of claim 1 wherein said isomerization catalyst is ruthenium chloride hydrate and said alk-2-enyl glycidyl ether is allyl glycidyl ether.

4. The process of claim 1 or 3 wherein said phase transfer catalyst is tetrabutyl ammonium bromide and the reaction with carbon dioxide is carried out above atmospheric pressure.

5. The process of claim 1, 2, 3, or 4 wherein said isomerization is carried out at reflux temperature under atmospheric pressure.

6. The process of any one of the above claims wherein said reaction with carbon dioxide is carried out at a temperature of between about 115° C. and about 135° C. under from about 75 to about 300 psig.

* * * * *

UNITED STATES PATENT OFFICE
CERTIFICATE OF CORRECTION

Patent No. 5,095,124                   Dated March 10, 1992

Inventor(s) Jeffrey S. Plotkin, Mark M. Miller, Paul D. Taylor

It is certified that error appears in the above-identified patent and that said Letters Patent is hereby corrected as shown below:

In the ABSTRACT, second line after the formula, please correct the following phrase to read:

--- n has a value of from 0 to 4 and n' has a value of from 1 to 4, ---

Signed and Sealed this

First Day of June, 1993

Attest:

MICHAEL K. KIRK

Attesting Officer    Acting Commissioner of Patents and Trademarks